United States Patent [19]
Brodkin et al.

[11] Patent Number: 6,155,830
[45] Date of Patent: Dec. 5, 2000

[54] DENTAL RESTORATIONS

[75] Inventors: Dmitri Brodkin, West Orange; Carlino Panzera, Bellemead; Paul Panzera, Mt. Holly; Jana Pruden, Bellemead; Lisa M. Kaiser, Monmouth Junction; Richard A. Brightly, South Brunswick, all of N.J.

[73] Assignee: Jeneric/Pentron Incorporated, Wallingford, Conn.

[21] Appl. No.: 09/190,475

[22] Filed: Nov. 12, 1998

Related U.S. Application Data

[63] Continuation of application No. 09/133,582, Aug. 13, 1998.
[60] Provisional application No. 60/091,527, Jul. 2, 1998, provisional application No. 60/088,866, Jun. 11, 1998, provisional application No. 60/077,555, Mar. 11, 1998, and provisional application No. 60/077,378, Mar. 10, 1998.

[51] Int. Cl.$^7$ .................................................. A61C 13/08
[52] U.S. Cl. ................... 433/212.1; 433/218; 433/222.1; 428/697; 428/699; 428/702; 106/35
[58] Field of Search ................................. 106/35; 501/57, 501/70, 59, 63, 72, 14; 428/697, 699, 701, 702; 433/218, 212.1, 222.1

[56] References Cited

U.S. PATENT DOCUMENTS

| | | | |
|---|---|---|---|
| 3,052,982 | 9/1962 | Weinstein et al. | 32/8 |
| 4,455,383 | 6/1984 | Panzera | 501/6 |
| 4,604,366 | 8/1986 | Kacicz et al. | 501/6 |
| 4,798,536 | 1/1989 | Katz | 433/212.1 |
| 5,173,114 | 12/1992 | Heurtaux | 106/35 |
| 5,314,334 | 5/1994 | Panzera et al. | 433/206 |
| 5,614,330 | 3/1997 | Panzera et al. | 428/697 |
| 5,622,551 | 4/1997 | Erbe et al. | 106/35 |
| 5,653,791 | 8/1997 | Panzera et al. | 106/35 |
| 5,698,019 | 12/1997 | Frank et al. | 106/35 |
| 5,713,994 | 2/1998 | Kramer et al. | 106/35 |

FOREIGN PATENT DOCUMENTS

| | | |
|---|---|---|
| 0 272 745 | 6/1988 | European Pat. Off. . |
| 0 544 145 | 6/1993 | European Pat. Off. . |
| 0 695 726 | 2/1996 | European Pat. Off. . |
| 0 795 311 | 9/1997 | European Pat. Off. . |
| WO 97 30678 | 8/1997 | WIPO . |

*Primary Examiner*—Deborah Jones
*Assistant Examiner*—Stephen Stein
*Attorney, Agent, or Firm*—Ann M. Knab

[57] ABSTRACT

A dental restoration comprising a porcelain composition, comprising a glassy matrix and leucite crystallites embedded therein, and having maturing temperatures in the range from about 680° C. to about 870° C. and CTEs in the range from about 12 to about 15, more preferably in the range from about 12.5 to about 14.5, and most preferably in the range from about 13.1 to about $14.5 \times 10^{-6}$/° C. (measured from 25° C. to 470° C.). The porcelain is used in combination with a ceramic core or metal framework. The ceramic core comprises cubic leucite and exhibits maturing temperatures less than about 1200° C. and CTEs in the range of about 12.5 to about $15.0 \times 10^{-6}$/° C. (measured from 25° C. to 500° C.).

6 Claims, No Drawings

DENTAL RESTORATIONS

CROSS-REFERENCE TO RELATED APPLICATIONS

This application is a continuation of U.S. patent application Ser. No. 09/133,582, filed Aug. 13, 1998, which claims priority to U.S. Provisional Application No. 60/091,527, filed Jul. 2, 1998, U.S. Provisional Application No. 60/088,866, filed Jun. 11, 1998, U.S. Provisional Application No. 60/077,555, filed Mar. 11, 1998, and U.S. Provisional Application No. 60/077,378 filed Mar. 10, 1998, all which are incorporated herein by reference.

BACKGROUND OF THE INVENTION

1. Field of the Invention

The present invention relates to dental restorations fabricated of low-fusing overlay porcelain and to porcelain having dual use for all-ceramic and porcelain-fused-to-metal ("PFM") restorations and to dental restorations fabricated of all-ceramic cores comprising cubic leucite.

2. Brief Description of the Related Art

Porcelain dental restorations, such as crowns, bridges, and the like are highly favored because the porcelains provide strength, wear resistance, and favorable aesthetics. Older porcelain restorations generally comprise at least one porcelain layer on a metal framework, commonly known as PFM restorations. Typically, PFM restorations are fabricated by applying a dental porcelain powder in aqueous slurry to a metal alloy framework, then firing the porcelain at high temperature to form a tight, impervious porcelain layer having the appearance of natural dentition. Those skilled in the art recognize that it is important that the firing temperature of the porcelain be at least 100° C. below the solidus temperature of the alloy used as the metal framework, to prevent melting or distortion of the metal framework. For example, selected gold alloys having gold contents above 70 percent exhibit solidus temperatures of about 900° C. and require overlay porcelain having sufficiently low firing temperatures. It is further important that the coefficient of thermal expansion (CTE) of the porcelain be only slightly less than that of the metal so that no cracks are produced in the porcelain layer due to thermal expansion mismatch stress occurring during firing and cooling down. Metal alloys heretofore employed in the manufacture of dental restorations have typically possessed moderately high coefficients of thermal expansion ranging from about $13 \times 10^{-6}/°$ C. to about $15 \times 10^{-6}/°$ C., with the exception of titanium and some gold-based alloys which have coefficients of thermal expansion of about $9 \times 10^{-6}/°$ C. and $16-17.5 \times 10^{-6}/°$ C., respectively.

In commonly assigned U.S. application Ser. No. 08/532,179 filed Sep. 22, 1995, now abandoned, the contents of which are incorporated by reference herein, a dental porcelain composition is described which is amorphous, i.e., single phase, and which possesses a moderately high coefficient of thermal expansion closely matching those of conventional alloys and some ceramics heretofore employed in the manufacture of dental restorations. This composition is advantageously applied to such conventional alloys to provide an extremely smooth, fused glassy surface on the resulting dental restoration. Newer restorations, however, generally comprise a ceramic core in place of the traditional metal, with at least one additional porcelain layer. These are commonly referred to as "all-ceramic" systems, and can provide even better aesthetics than the metal-porcelain systems. Among all-ceramic systems, high strength porcelains provide a more natural translucency and therefore much improved aesthetics. Dental ceramics exhibit a wide range of coefficients of thermal expansion, from as low as about $8 \times 10^{-6}/°$ C. (e.g., alumina) to as high as about $18 \times 10^{-6}/°$ C. (e.g., some leucite-reinforced ceramics).

Among the commercially-available all-ceramic systems, many are based on pressable, high-strength feldspathic porcelains, for example pressable leucite-reinforced porcelains commercially available under the trade name "OPC®" from Jeneric®/Pentron®, Inc. (Wallingford, Conn.). These feldspathic glass-ceramics comprise from about 40% to 50% of a discontinuous, evenly dispersed, tetragonal potassium leucite phase, which imparts strength to the dental restoration. Leucite is a crystalline potassium aluminum silicate ($K_2O.Al_2O_3.4SiO_2$) which ordinarily has a tetragonal crystal structure at room temperature. Use of tetragonal leucite, also known as "low leucite", is described for reinforcement of feldspathic dental porcelains in U.S. Pat. No. 3,052,982 to Weinstein et al., U.S. Pat. No. 4,604,366 to Kacicz et al., U.S. Pat. No. 4,798,536 to Katz, and U.S. Pat. No. 5,614,330 to Panzera, the entire contents of the foregoing patents being incorporated herein by reference. While well-suited for their intended purposes, prior art porcelains for all-ceramic restorations are available in a limited range of maturing temperatures and CTEs, and contain leucite having at least some coarse-grained morphology, that is, a distribution of grain sizes wherein at least a fraction of the grains are greater than about 10 microns, or even greater than about 20 microns. Such coarse-grained leucite can wear away the opposing natural dentition in the mouth.

There accordingly remains a need in the art for dual purpose porcelain systems wherein the maturing temperature is low enough to match that of metal frameworks, including gold alloys and porcelain cores, and even more advantageously, wherein the CTE may be adjusted to match a range of metal substructure or all ceramic cores. There particularly remains a need for high-strength porcelain systems having low maturing temperatures, yet moderately high CTEs, and having a fine-grained leucite crystal structure for reducing wear of the opposing natural dentition. Such porcelains must farther be simple and inexpensive to manufacture.

SUMMARY OF THE INVENTION

The above-described drawbacks and deficiencies of the prior art are alleviated by the low-fusing dental porcelain compositions of the present invention comprising a glassy matrix and tetragonal leucite dispersed therein, and having maturing temperatures in the range from about 680° C. to about 870° C. and more preferably in the range from about 730° C. to about 770° C., and CTEs in the range from about 12 to about $15 \times 10^{-6}/°$ C., more preferably in the range from about 12.5 to about $14.5 \times 10 hu -6/°$ C., and most preferably in the range from about 13.1 to about $14.5 \times 10^{-6}/°$ C. (measured from 25° C. to 470° C.). The tetragonal leucite in accordance with the present invention is preferably both fine-grained (i.e, having average diameters of less than about 5 microns) and uniformly-sized. The compositions are described in more detail below.

The low-fusing dental porcelain compositions are used in combination with a metal or all ceramic core. The metal core can be made from commercially available alloys having expansion in the range of about $13.2-15.1 \times 10^{-6}/°$ C. and a solidus temperature above about 900° C.

The all-ceramic cores of the present invention exhibit maturing temperatures preferably less than 1200° C. and most preferably in the range of about 900° C. to about 1200° C. The CTEs of the all-ceramic cores are preferably in the range of from about 12.5 to about 15.0×10$^{-6}$/° C. (measured from 25° C. to 500° C.) and more preferably in the range from about 13.0 to about 14.0×10$^{-6}$/° C. (measured from 25° C. to 500° C.) and are most preferably about 13.8×10$^{-6}$/° C. (measured from 25° C. to 470° C.). These cores are pressable at temperatures not exceeding 1150° C.

In one embodiment of the method of the present invention, a porcelain frit comprising fine grain sized tetragonal leucite is combined with at least one frit having a low maturing temperature in order to produce the porcelain of the present invention. In another embodiment of the method of the present invention, the fine grain sized tetragonal leucite is crystallized from a single glassy frit in the initially amorphous glass by heat-treatment of this starting amorphous glass powder. Restorations are produced comprising the metal framework or all-ceramic core of the present invention in combination with the overlay porcelain of the present invention.

DETAILED DESCRIPTION OF THE INVENTION

The present invention is directed to a low-fusing overlay porcelain comprising a glassy matrix and tetragonal leucite, and having maturing temperatures in the range from about 680° C. to about 870° C. and more preferably in the range from about 730° C. to about 770° C., and coefficients of thermal expansion in the range from about 12 to about 15×10$^{-6}$/° C. (measured from 25° C. to 470° C.), more preferably in the range from about 12.5 to about 14.5×10$^{-6}$/° C. (measured from 25° C. to 470° C.) and most preferably in the range from about 13.1 to about 14.5×10$^{-6}$/° C. (measured from 25° C. to 470° C.).

The tetragonal leucite in the overlay porcelain of the present invention is preferably both fine-grained and uniformly-sized, in order to minimize wear to the opposing dentition. By "fine-grained" is meant leucite crystallites having average diameters of less than or equal to about five microns, preferably less than or equal to about three microns, and most preferably less than or equal to about two microns. Individual leucite grains having greater diameters may of course be present, but the presence of such grains is preferably minimized. As used herein, "diameters" refers to the longest single dimension of the crystallite, regardless of the shape of the crystallite.

The amount of leucite present in the glassy matrix is effective to achieve maturing temperatures in the range from about 680° C. to about 870° C. and coefficients of thermal expansion in the range from about 12 to about 15×10$^{-6}$/° C. (measured from 25° C. to 470° C.), and is empirically determined by means known in the art, depending on the size and distribution of the tetragonal leucite, the composition of the glassy matrix, the desired maturing temperature and the coefficient of thermal expansion. Generally, the leucite is present in an amount in the range from about 0% to about 20% by weight of the total composition, and preferably is present in an amount less than about 10% by weight of the total composition. As is mentioned below, inclusion of cesium in the glass composition will minimize the amount of leucite required in order to achieve a higher coefficient of thermal expansion.

In one embodiment of the method of manufacture of the present invention, a first porcelain component comprising fine grain sized tetragonal leucite is combined with at least one second porcelain component having a very low maturing temperature, for example in the range from about 600° C. to about 760° C. The composition of the first porcelain component and the at least one second porcelain component is such that combination of the first and second porcelain compositions yields the compositions given in Table 1 below. In general, use of at least two porcelain components, or frits, allows greater control in fine-tuning the coefficient of thermal expansion and maturing temperature of the porcelain composition.

The tetragonal leucite for the first porcelain component may be synthesized by means known in the art, for example by volume crystallization. Thus a mixture of powdered metal oxides, carbonates, nitrates and other precursor materials known in the art in the appropriate proportions are blended, for example by ball milling for one to three hours. Nucleation agents such as $P_2O_5$, Pt, combinations of MgO, ZnO, $TiO_2$ and the like are optionally added to the metal oxides and/or carbonates before blending in order to control nucleation density. The blended powders are then melted to form a homogeneous glass melt, the glass is quenched (in water or by other means,) and then heated to an elevated temperature (e.g., 950–1100° C.) for up to six hours, allowing the formation and growth of the crystalline leucite. Alternatively, the powders are melted to form a homogeneous glass melt, then directly cooled to the crystallization temperature without intermediate quenching. After leucite formation, the material is then quenched, crushed, and reduced to a fine powder. Volume crystallization is known in the art, being described for example in U.S. Pat. No. 4,455,383 to Panzera and U.S. Pat. No. 4,798,536 to Katz, the contents of which patents are incorporated by reference herein.

Alternatively, the leucite-containing porcelain component may be formed by surface crystallization, wherein a mixture of powdered metal oxides, carbonates, nitrates and other known precursor materials in the appropriate proportions (and optional nucleation agents) are blended, for example by ball milling for one to three hours. The powders are then fused to form a glass melt, which is quenched in water or by other means. The quenched glass is then milled to a powder before subjecting the powder to heat treatment in order to effect crystallization of leucite.

In a second embodiment of the method of the present invention, the dental porcelains are formed by volume or powder crystallization of fine grained leucite from a single porcelain composition as described in connection with the first porcelain component above.

Compositional ranges for the fine grained leucite porcelains in accordance with the present invention are shown in Table 1 below.

TABLE 1

|           | Range (wt. %) |        |
|-----------|---------------|--------|
| Component | 1             | 2      |
| $SiO_2$   | 40–65         | 57–65  |
| $Al_2O_3$ | 6–12          | 7–12   |
| $K_2O$    | 5–15          | 7–14.5 |
| $Na_2O$   | 6–12          | 7–12   |
| $Li_2O$   | 0–3           | 0.3–3  |
| $B_2O_3$  | 0–4           | *      |
| BaO       | 0–2           | 0–2    |
| CaO       | 0–3           | 0–3    |
| MgO       | 0–4           | 0–4    |
| $Cs_2O$   | 0–5           | 0–5    |
| F         | 0–2           | 0–2    |

TABLE 1-continued

| | Range (wt. %) | |
|---|---|---|
| Component | 1 | 2 |
| $P_2O_5$ | 0–3 | 0–3 |
| $CeO_2$ | 0–1 | 0–1 |
| $Sb_2O_3$ | 0–1 | 0–1 |
| Acidic flux[1] | 0.8–4 | 0.8–4.0 |
| Alkaline flux[2] | 6–15 | 7.3–15 |
| Additives[3] | 0–50 | 0–5 |

* Component excluded from composition except as unavoidable and unintended contamninant
[1] $B_2O_3$ + F + $P_2O_5$
[2] $Li_2O$ + $Na_2O$
[3] Pigments, opacifying agents, fluorescing agents The properties of the porcelain components and compositions can be adjusted by applying well known principles. For example, the coefficient of thermal expansion can be increased, if desired, by increasing the leucite content, and by decreasing the proportion of $SiO_2$ and/or increasing the proportion of the alkali metal oxides. Addition of small quantities of $Cs_2O$, wherein the molar ratio of $Cs_2O/K_2O$ is less than 0.1, may significantly increase the expansion of the resulting porcelain. Accordingly, the leucite content is adjusted downward in order to obtain the same CTE. The presence of the acidic fluxes, that is, $B_2O_3$, $P_2O_5$ or F or their combination wherein $B_2O_3+F+P_2O_5=0.8-4\%$ by weight is necessary to attain the requisite crystallization parameters and/or to lower the maturing temperatures. Alkaline fluxes refers to the total quantity of $Li_2O+Na_2O$.

The overlay porcelain in accordance with the present invention comprises or may further comprise other additives known in the art, such as opacifiers, pigments (e.g., chromates, vanadates, and manganates, and the like) and fluorescing agents (e.g., $Tb_2O_5$, $Y_2O_3$, and the like)

In one embodiment of the invention, a composition for an all-ceramic core is provided which is compatible with overlay porcelain compositions of the present invention. The compositional ranges are provided in Table 2 below. The core compositions are preferably produced from a combination of feldspar and fluxing agents or, alternatively, from a mixture of individual oxide precursor materials. The core porcelain obtained may be heat-pressed into a desired shape at temperatures not exceeding about 1150° C. Alternatively, the all-ceramic core may be consolidated from powder by condensing the powder onto a refractory die and sintering it at maturing temperatures of less than about 1200° C.

TABLE 2

| COMPONENT | RANGE mole % |
|---|---|
| $SiO_2$ | 60–75 |
| $B_2O_3$ | 0–5 |
| $Al_2O_3$ | 11.7–13.0 |
| MgO | 0–3 |
| CaO | 0–3 |
| BaO | 0–2 |
| $Li_2O$ | 0–3 |
| $K_2O$ | 8.0–9.7 |
| $Cs_2O$ | 1–2 |
| $Na_2O$ | 0–5 |
| F | 0–5 |
| $P_2O_5$ | 0–2 |
| CTE (25° C.–470° C.) | — |
| CTE (25° C. to 500° C.) | 12.5–15.0 |

The following example illustrates fabrication of a ceramic core material in accordance with the present invention.

EXAMPLE A

Material for an all ceramic core was produced by mixing 90.75 weight percent of feldspar with 7.25 weight percent of $Cs_2CO_3$ and 2 weight percent $Li_2CO_3$. The mixture was melted at 1200° C. to produce a glass ceramic material. The resulting glass ceramic material was then cooled and pulverized. The leucite phase in the obtained material was substantially fine-grained and almost completely devoid of dendritic features. The composition set forth in Table 3 below represents the glass-ceramic produced. The glass ceramic material was milled into powder and sieved to –200 mesh. The powder was used to fabricate 2 gram pellets that were heat-pressed to form all-ceramic rods that were tested to determine flexural strength. Twelve bars were tested for each temperature. The various pressing temperatures and corresponding flexural strengths are listed in Table 3 below.

TABLE 3

| COMPONENT | EXAMPLE A mole % (wt. %) |
|---|---|
| $SiO_2$ | 72.5 (61.2) |
| $B_2O_3$ | — |
| $Al_2O_3$ | 11.9 (17.0) |
| MgO | — |
| CaO | 0.9 (0.7) |
| BaO | — |
| $Li_2O$ | 2.0 (0.8) |
| $K_2O$ | 9.2 (12.1) |
| $Cs_2O$ | 1.6 (6.4) |
| $Na_2O$ | 2.0 (1.7) |
| F | — |
| $P_2O_5$ | — |
| CTE (25° C.–470° C.) | 13.8 |
| CTE (25° C. to 500° C.) | 13.7 |

TABLE 4

| PRESSING TEMPERATURE | FLEXURAL STRENGTH (MPa) AVERAGE | STANDARD DEVIATION |
|---|---|---|
| 1175° C. | 128 | 14 |
| 1150° C. | 150 | 16 |
| 1140° C. | 118 | 10 |
| 1110° C. | 113 | 10 |
| 1100° C. | 109 | 15 |

In a further embodiment, the porcelain composition of the present invention is fused to a metal alloy framework or all-ceramic core described hereinbefore to provide a coating thereon. Suitable alloys include those known in the art having a coefficient of thermal expansion in the range from about 13.2 to about $15.1 \times 10^{-6}/°$ C., or preferably in the range from about 13.6 to about $14.9 \times 10^{-6}/°$ C. Such restorations commonly have multiple porcelain layers in order to simulate natural teeth, and the porcelain of this invention may be used in any one or a combination of these layers, although it is preferably used as an overlayer. The porcelain layers are applied in the conventional manner, that is, in the form of a paste of the porcelain powder in water over the framework, shaping to the desired shape, and then firing.

In another embodiment, the porcelain is used to fabricate inlays, onlays, or veneers to replace amalgam, gold, or other porcelains. In this embodiment, the core porcelain powder in accordance with the present invention is built on a refractory die (for example, the refractory die available from Jeneric/Pentron Inc., Wallingford, Conn. under the trade name SYNVEST™) in the form of an aqueous slurry, and then fired to an appropriate temperature to effect maturation and maturing of the porcelain In yet another embodiment of the invention, a method of determining compatibility between the core material and the overlay porcelain is provided for the fabrication of dental restorations. The selection of the overlay porcelain for the all-ceramic core material is determined by comparing curves of the core material and the overlay porcelain. The overlay porcelain is chosen among candidates with the middle point of the softening range not exceeding 480° C. Middle of Softening Range=(Transition Temperature+Dilatometic Softening Temperature)/2. Softening range is defined for this purpose as the range of temperatures between the glass transition temperature and the dilatometric softening temperature. It has been found that the best results for compatibility are achieved when the thermal expansion curve for the overlay porcelain touches tangentially the thermal expansion curve for the all-ceramic core material within the upper half of the softening range of the overlay porcelain as shown in the FIG. 1. Small deviations from this empirical rule are acceptable, however, at its dilatometric softening temperature the overlay porcelain should match the expansion of the core within $\pm 2 \times 10^{-6}/°$ C. The overlay porcelain preferably has transition temperatures not exceeding 440° C. and softening temperatures not exceeding 520° C.

The following compositions (percent by weight) set forth in Table 5 are exemplary of the compositions of the dental porcelains of the present invention.

TABLE 5

| Component | Ex. 1 | Ex. 2 |
|---|---|---|
| $SiO_2$ | 63.7 | 63.7 |
| $Al_2O_3$ | 9.9 | 9.7 |
| $K_2O$ | 11.0 | 11.5 |
| $Na_2O$ | 10.7 | 10.3 |
| $Li_2O$ | 1.2 | 1.3 |
| $B_2O_3$ | — | — |
| BaO | — | — |
| CaO | 1.7 | 1.8 |
| MgO | 0.9 | 1.0 |
| F | 1.3 | 1.3 |
| $Cs_2O$ | — | — |
| $CeO_2$ | — | — |
| $Sb_2O_3$ | — | 0.4 |
| Pigments, Opacifiers | — | 0.50 |
| CTE* | 13.8 | 13.8 |
| Maturing T, ° C. | 730–740 | 730–740 |
| Wt. % leucite** | 5 | 5 |

*$\times 10^{-6}/°$ C. measured over 25° C. to 470° C. $\pm 0.7 \times 10^{-6}/°$ C.

The above compositions were calculated based on starting batch compositions. Actual fluorine content may therefore be significantly lower due to volatilization losses during melting. The exact percentages of other components such as $Li_2O$ and $B_2O_3$ may also deviate slightly from these calculated values. Other components may or may not be present depending on the particular use and physical requirements of the porcelain.

The exact CTEs of porcelains of course depend on the range over which the measurements are made. For example, the CTEs for Examples 1 and 2 are about 12.5 (measured over 25–400° C.), about 12.7 (measured over 25–430° C.), about 13.8 (measured over 25–470° C.), and about 14.6 (measured over 25–500° C.). Thus, the porcelains of Examples 1 and 2 are matched to alloys having expansions in the range from about $13.6–14.9 \times 10^{-6}/°$ C., as well as all-ceramic cores having expansions in the range of 13.0 to $14.0 \times 10^{-6}/°$ C. (measured over 25–500° C.).

The following examples illustrate restorations made in accordance with the present invention.

EXAMPLE B

The glass ceramic powder produced in Example A was formed into a series of cores and was overlaid with unshaded porcelain from Example 1 of Table 4 using conventional wet condensation techniques. The porcelain was fired at 1350° F. at 75° F./min and the resulting restoration exhibited good bonding and did not show signs of cracking, delamination or crazing. Some of the crowns were additionally treated by grinding a portion of the surface thereof. Porcelain was then applied to the surface which had been treated and the crowns were refired up to five times at temperatures 10° F.–20° F. below the temperature of the first firing. All of the crowns exhibited good bonding and did not show signs of cracking, delamination or crazing.

EXAMPLE C

Metal copings made from Rexillium® V and Biostar available from both available from Jeneric/Pentron Inc., Wallingford, Conn. were used to form metal copings. The CTEs of the materials were $13.9 \times 10^{-6}/°$ C. and $14.2 \times 10^{-6}/°$ C., respectively. The copings were opaqued with Synspar Add-On Opaque available from Jeneric/Pentron Inc., Wallingford, Conn. and applied according to the manufacturer's instructions. Overlay porcelain from Example 2 in Table 4 was applied to the opaque layer and the porcelain was fired at 1350° F. at 75° F./min. The resulting restoration exhibited good bonding and did not show signs of cracking, delamination or crazing. Some of the crowns were additionally treated by grinding a portion of the surface thereof. Porcelain was then applied to the surface which had been treated and the crowns were refired up to five times at temperatures 10° F.–20° F. below the temperature of the first firing. All of the crowns exhibited good bonding and did not show signs of cracking, delamination or crazing.

While various descriptions of the present invention are described above, it should be understood that various features can be used singly or in any combination thereof. Therefore, this invention is not to be limited to only the specifically preferred embodiment depicted herein. Further, it should be understood that variations and modifications within the spirit and scope of the invention may occur to those skilled in the art to which the invention pertains. Accordingly, all expedient modifications ready attainable by one versed in the art from the disclosure set forth herein that are within the scope and spirit of the present invention are to by included as further embodiments of the present invention. The scope of the present invention is accordingly defined as set forth in the appended claims.

What is claimed is:

1. A dental restoration comprising:
   a dental porcelain powder from a dental composition comprising 40–65% $SiO_2$, 6–12% $Al_2O_3$, 5–15% $K_2O$, and 6–12% $Na_2O$, 0–3% $Li_2O$, 0–4% $B_2O_3$, 0–2% F, and 0–3% $P_2O_5$ by weight of the total composition, wherein the weight percent of $(F+B_2O_3+P_2O_5)$ is in the range from 0.8–4.0 and the weight percent of $(Li_2O+Na_2O)$ is in the range from 6–15, and wherein the porcelain comprises a glassy matrix phase and a leucite crystallite phase, wherein the leucite phase comprises from about 0 to about 20% by weight of the total composition and the leucite crystallites have average diameters of less than about 5 microns; and further wherein the porcelain has a maturing temperature in the range from about 680° C. to about 870° C. and a coefficient of thermal expansion in the range from about 12 to about $15 \times 10^{-6}/°$ C. (measured from 25° C. to 470° C.);

a ceramic core, wherein the ceramic core comprises 60–75% $SiO_2$, 11.7–13.0% $Al_2O_3$, 8–9.7% $K_2O$ and 1–2% $Cs_2O$ in mole percent of the total composition; and wherein the ceramic core exhibits a coefficient of thermal expansion in the range from about 12.5 to about $15 \times 10^{-6}/°$ C. (measured from 25° C. to 500° C.) and the metal framework exhibits a coefficient of thermal expansion in the range from about 13.2 to about $15.1 \times 10^{-6}/°$ C. (measured from 25° C. to 500° C.).

2. The restoration of claim 1 wherein the ceramic core further comprises up to 3% $Li_2O$, up to 5% $B_2O_3$, up to 5% F, up to 2% $P_2O_5$ up to 3% MgO, up to 3% CaO, up to 5% $Na_2O$ and up to 2% BaO in mole percent of the total composition.

3. The restoration of claim 1 wherein the dental porcelain composition further comprises a component selected from the group consisting of pigments, opacifiers, fluorescing agents, and mixtures thereof in an amount up to 50% by weight of the composition.

4. A dental restoration comprising:

a dental porcelain powder from a dental composition comprising 57–65% $SiO_2$, 7–12% $Al_2O_3$, 7–14.5% $K_2O$, and 7–12% $Na_2O$, 0.3–3% $Li_2O$, 0–2% F, and 0–3% $P_2O_5$ by weight of the total composition, wherein the weight percent of $(F+B_2O_3+P_2O_5)$ is in the range from 0.8–4.0 and the weight percent of $(Li_2O+Na_2O)$ is in the range from 7.3–15, and wherein the porcelain comprises a glassy matrix phase and a leucite crystallite phase, wherein the leucite phase comprises from about 0 to about 20% by weight of the total composition and the leucite crystallites have average diameters of less than about 5 microns; and further wherein the porcelain has a maturing temperature in the range from about 680° C. to about 870° C. and a coefficient of thermal expansion in the range from about 12 to about $15 \times 10^{-6}/°$ C. (measured from 25° C. to 470° C.);

a ceramic core, wherein the ceramic core comprises 60–75% $SiO_2$, 11.7–13.0% $Al_2O_3$, 8–9.7% $K_2O$ and 1–2% $Cs_2O$ in mole percent of the total composition; and wherein the ceramic core exhibits a coefficient of thermal expansion in the range from about 12.5 to about $15 \times 10^{-6}/°$ C. (measured from 25° C. to 500° C.) and the metal framework exhibits a coefficient of thermal expansion in the range from about 13.2 to about $15.1 \times 10^{-6}/°$ C. (measured from 25° C. to 500° C.).

5. The restoration of claim 4 wherein the ceramic core further comprises up to 3% $Li_2O$, up to 5% $B_2O_3$, up to 5% F, up to 2% $P_2O_5$ up to 3% MgO, up to 3% CaO, up to 5% $Na_2O$ and up to 2% BaO in mole percent of the total composition.

6. The restoration of claim 4 wherein the dental porcelain composition further comprises a component selected from the group consisting of pigments, opacifiers, fluorescing agents, and mixtures thereof in an amount up to 5% by weight of the composition.

* * * * *